US012642778B2

(12) United States Patent
Li et al.

(10) Patent No.: US 12,642,778 B2
(45) Date of Patent: Jun. 2, 2026

(54) USE OF MITOXANTRONE HYDROCHLORIDE LIPOSOME AND CYCLOPHOSPHAMIDE, VINCRISTINE AND PREDNISONE

(71) Applicant: CSPC Zhongqi Pharmaceutical Technology (Shijiazhuang) Co., Ltd., Shijiazhuang (CN)

(72) Inventors: Chunlei Li, Shijiazhuang (CN); Xuefang Xia, Shijiazhuang (CN); Yanhui Li, Shijiazhuang (CN); Na An, Shijiazhuang (CN); Yanling Du, Shijiazhuang (CN); Tong Li, Shijiazhuang (CN); Shixia Wang, Shijiazhuang (CN); Runlu Jia, Shijiazhuang (CN)

(73) Assignee: CSPC Zhongqi Pharmaceutical Technology (Shijiazhuang) Co., Ltd, Shijiazhuang (CN)

( * ) Notice: Subject to any disclaimer, the term of this patent is extended or adjusted under 35 U.S.C. 154(b) by 463 days.

(21) Appl. No.: 18/023,161

(22) PCT Filed: Aug. 26, 2021

(86) PCT No.: PCT/CN2021/114810
§ 371 (c)(1),
(2) Date: Feb. 24, 2023

(87) PCT Pub. No.: WO2022/042653
PCT Pub. Date: Mar. 3, 2022

(65) Prior Publication Data
US 2024/0024257 A1     Jan. 25, 2024

(30) Foreign Application Priority Data

Aug. 27, 2020     (CN) ......................... 202010878461.4

(51) Int. Cl.
| | |
|---|---|
| *A61K 31/136* | (2006.01) |
| *A61K 9/00* | (2006.01) |
| *A61K 9/1271* | (2025.01) |
| *A61K 31/475* | (2006.01) |
| *A61K 31/573* | (2006.01) |
| *A61K 31/664* | (2006.01) |
| *A61P 35/00* | (2006.01) |

(52) U.S. Cl.
CPC .......... *A61K 31/136* (2013.01); *A61K 9/0019* (2013.01); *A61K 9/1271* (2013.01); *A61K 31/475* (2013.01); *A61K 31/573* (2013.01); *A61K 31/664* (2013.01); *A61P 35/00* (2018.01)

(58) Field of Classification Search
CPC .. A61K 31/136; A61K 9/0019; A61K 9/1271; A61K 31/475; A61K 31/573; A61K 31/664; A61P 35/00
See application file for complete search history.

(56) References Cited

U.S. PATENT DOCUMENTS

2013/0243861 A1     9/2013   Roy et al.

FOREIGN PATENT DOCUMENTS

| | | |
|---|---|---|
| CN | 101209243 A | 7/2008 |
| CN | 110711178 A | 1/2020 |
| WO | 1999/55375 A1 | 11/1999 |

OTHER PUBLICATIONS

Ma et al.; 614.Acute Lymphoblastic Leukemias: Therapies, Excluding Transplantation and Cellular Immunotherapies; Blood, 142 (2023) 5897-5898. (Year: 2023).*
Advani et al.; A phase II study of cyclophosphamide, etoposide, vincristine, and prednisone (CEOP); British Journal of Haematology, 2016, 172, 535-544. (Year: 2016).*
Marquardt et al.; Substitution of mitoxantrone for doxorubicin in a multidrug chemotherapeutic protocol for first-line treatment of dogs with multicentric intermediate- to large-cell lymphoma; J. Am. Vet. Med. Association., 2019, 254, 236-242. (Year: 2019).*
Li et al.; Pegylated liposomal mitoxantrone is more therapeutically active thanmitoxantrone in L1210 ascitic tumor and exhibits dose-dependentactivity saturation effect; Int. J. of Pharmaceutics, 2014, 460, 165-172. (Year: 2014).*
Chen et al.; Influence of lipid composition on the phase transition temperature of liposomes composed of both DPPC and HSPC; Drug Dev. and Ind. Pharm., 2013; 39(2): 197-204. (Year: 2013).*
Huang, Safety and Efficacy of Mitoxantorone Hydrochloride Liposome in Patients with Relapsed or Refractory Peripheral T-Cell Lymphoma and Extranodal NK/T-Cell Lymphoma: A Multicenter, Single-Arm, Open-Label, Phase 2 Clinical Trial. Blood. Nov. 13, 2019;134(Suppl. 1):2838.
Indzhikyan, Directory Vidal, Medications in Russia, Sixteenth Edition. CMPMedica, vidal@ru.cmpmedica.com. p. B-419, (2010).
Nyhammar et al., Dissolution time for three formulations of cyclophosphamide powder for injection. Acta Oncol. 1991;30(7):867.
Schmitz et al., Treatment and prognosis of mature T-cell and NK-cell lymphoma: an analysis of patients with T-cell lymphoma treated in studies of the German High-Grade Non-Hodgkin Lymphoma Study Group. Blood. Nov. 4, 2010;116(18):3418-25.

(Continued)

*Primary Examiner* — Sarah Pihonak
*Assistant Examiner* — Jackson J Hernandez
(74) *Attorney, Agent, or Firm* — McCarter & English, LLP; Wei Song

(57)     ABSTRACT

The use of a mitoxantrone hydrochloride liposome and cyclophosphamide, vincristine and prednisone in the preparation of a drug for treating peripheral T-cell lymphoma (PTCL). The PTCL is preferably treatment-naïve PTCL. Other first-line and second-line drugs for treating PTCL may also be further used on the basis of the foregoing. A method for treating PTCL, the method comprising administering, to a patient, a therapeutically effective amount of a mitoxantrone hydrochloride liposome and cyclophosphamide, vincristine and prednisone. The combined administration of the drugs is safe and tolerable, has a small toxicity and few side effects, and can obtain a higher total objective remission rate (ORR) in treatment-naïve PTCL patients.

8 Claims, No Drawings

(56)                    References Cited

OTHER PUBLICATIONS

Peters et al., Treatment of elderly patients with intermediate- and high-grade non-Hodgkin's lymphoma: a retrospective population-based study. Ann Hematol. Mar. 2001;80(3):155-9.
Sonneveld et al., Full dose chemotherapy in elderly patients with non-Hodgkin's lymphoma: a feasibility study using a mitoxantrone containing regimen. Br J Cancer. Jul. 1990;62(1):105-8.
Zhu et al., Analysis of a Curative Effect in Treatment of Non-Hodgkin Lymphoma by an E(M)COP Chemotherapy Regimen. China Journal of Modern Medicine. Nov. 30, 2001;11(11):58-9.
International Search Report and Written Opinion for Application No. PCT/CN2021/114810, dated Nov. 29, 2021, 14 pages.
Yang et al., Phase I clinical trial of pegylated liposomal mitoxantrone plm60-s: pharmacokinetics, toxicity and preliminary efficacy. Cancer Chemother Pharmacol. Sep. 2014;74(3):637-46.

* cited by examiner

USE OF MITOXANTRONE HYDROCHLORIDE LIPOSOME AND CYCLOPHOSPHAMIDE, VINCRISTINE AND PREDNISONE

CROSS REFERENCE TO RELATED APPLICATIONS

This application is a U.S. National Stage Application filed under 35 U.S.C. § 371, based on International Patent Application No. PCT/CN2021/114810, filed on Aug. 26, 2021, which claims the priority to and the benefit of Chinese Patent Application No. 202010878461.4, filed on Aug. 27, 2020.

TECHNICAL FIELD

The present disclosure belongs to antitumor field, and specifically relates to use of a mitoxantrone hydrochloride liposome and cyclophosphamide, vincristine, and prednisone in the preparation of a medication for treating treatment-naïve peripheral T-cell lymphoma (PTCL).

BACKGROUND

PTCL is a group of lymphoproliferative tumors originating from mature post-thymic T cells with obvious heterogeneity, and most of them show aggressive invasiveness. According to the WHO classification standards revised in 2016 (Swerdlow S H, et al. The 2016 revision of the World Health Organization classification of lymphoid neoplasms. Blood. 2016 May 19; 127(20):2375-2390.), PTCL includes four major categories with a total of 30 or more subtypes, including peripheral T-cell lymphoma, not otherwise specified; angioimmunoblastic T-cell lymphoma; extranodal NK/T-cell lymphoma, nasal type; ALK+ systematic anaplastic large T-cell lymphoma; ALK– systematic anaplastic large T-cell lymphoma; mycosis fungoides/Sézary syndrome, etc., and the complicated pathological classification reflects the heterogeneity of this group of diseases. There are regional differences in terms of the incidence and distribution of pathological subtypes of PTCL. The incidence rate in Asia is slightly higher than those in Europe and the United States. In China, PTCL accounts for about 25% to 35% of non-Hodgkin's lymphoma (NHL), which is significantly higher than that (10% to 15%) in European and American countries.

Of note, the treatment of PTCL is not optimistic; the overall response rate of the first-line CHOP (cyclophosphamide, doxorubicin, vincristine, and prednisone) or CHOP-based regimens is not high, and PTCL is apt to relapse and has poor prognosis. Except for ALK+ systematic anaplastic large T-cell lymphoma (ALCL), other subtypes of PTCL merely have a 5-year survival rate of 14% to 32% (Vose J, et al. International peripheral T-cell and natural killer/T-cell lymphoma study: pathology findings and clinical outcomes. J Clin Oncol. 2008 Sep. 1; 26(25): 4124-4130).

There have been studies at home and abroad to explore the first-line efficacies of anthracycline-free regimens in the treatment of PTCL, but their efficacies have not yet been proven to be superior to those of the CHOP-based regimens (mainly based on anthracyclines). Therefore, the first-line status of anthracycline-containing regimens has not yet been shaken. It could be seen that there still remains a need to further explore a safe and effective first-line treatment regimen for PTCL.

Mitoxantrone hydrochloride is a kind of anthracyclines and has been used in more than 30 countries worldwide to date. It has therapeutic effects on hematological tumors such as acute leukemia and lymphoma and a plurality of solid tumors such as breast cancer. Its adverse reactions are mainly presented as myelosuppression, gastrointestinal reactions, and cardiotoxicity. Clinically, it is used mainly to treat acute myeloid leukemia.

Liposome is a new form of drug delivery. Studies have shown that liposome may change the in vivo distribution of encapsulated drug and enable the drug to accumulate primarily in tumor tissues, thereby improving the therapeutic index of the drug, reducing the therapeutic dose of the drug, and reducing drug toxicity. These characteristics draw great attention to the application of drug-loaded liposomes in studies on antitumor drugs. Researchers have studied the liposome preparations of mitoxantrone. For example, WO2008/080367A1 discloses a mitoxantrone liposome, the disclosure of which is incorporated herein by reference in its entirety. Studies have shown that compared with ordinary preparations of mitoxantrone, liposome preparations have lower toxicity (in particular cardiotoxicity) and are characterized by passively targeting tumor tissues, which improves the antitumor activity.

Dose-escalation exploration and PK/PD studies (phase I) of the liposome injection of mitoxantrone hydrochloride as monotherapy have already been accomplished in subjects with advanced solid tumors and subjects with lymphoma. According to the experimental results, the present product is safe and tolerable within the dose range of 6 to 30 mg/m$^2$, and shows some efficacy. The critical phase II study of the liposome injection of mitoxantrone hydrochloride as monotherapy is conducted in patients with relapsed/refractory PTCL, and the enrollment (n=108 cases, dosage: 20 mg/m$^2$) has been finished; at present, the objective remission rate (ORR) evaluated by the Independent Review Committee (IRC) and confirmed by the efficacy is 40.7%. In view of good therapeutic effects of the present product as monotherapy on patients with relapsed/refractory PTCL, this study is intended to explore the combined administration of the liposome injection of mitoxantrone hydrochloride in treatment-naïve PTCL patients.

SUMMARY

Unless otherwise specified, "treatment-naïve" used in the present disclosure fits the following definition:

"treatment-naïve" is defined as newly diagnosed without receiving any anti-lymphoma treatment.

"Mitoxantrone" includes mitoxantrone and its pharmaceutically acceptable salts. The pharmaceutically acceptable salts of the mitoxantrone are preferably mitoxantrone hydrochlorides. Mitoxantrone liposome is preferably a mitoxantrone hydrochloride liposome.

The present disclosure provides use of a mitoxantrone liposome and cyclophosphamide, vincristine, and prednisone in the preparation of a medication for treating PTCL.

The PTCL is preferably at least one selected from the following subtypes: peripheral T-cell lymphoma, not otherwise specified (PTCL-NOS), angioimmunoblastic T-cell lymphoma (AITL), ALK+ anaplastic large T-cell lymphoma (ALCL), and ALK– anaplastic large T-cell lymphoma (ALCL).

At the same time, the present disclosure provides use of a mitoxantrone liposome in the preparation of a medication for improving an efficacy of cyclophosphamide, vincristine, and prednisone in the treatment of PTCL.

The present disclosure further provides use of a combination of cyclophosphamide, vincristine, and prednisone in the preparation of a medication for improving an efficacy of a mitoxantrone liposome in the treatment of PTCL.

Furthermore, the present disclosure provides a medication for treating PTCL, comprising a mitoxantrone liposome and cyclophosphamide, vincristine, and prednisone.

The PTCL is preferably treatment-naïve PTCL. The mitoxantrone liposome is preferably a mitoxantrone hydrochloride liposome.

Preferably, the mitoxantrone hydrochloride liposome, the prednisone, the cyclophosphamide, and the vincristine may be present in the same preparation or in separate preparations. When the four drugs described above are present in separate preparations, their dosage forms may or may not be the same. The dosage forms may be any clinically acceptable dosage form, e.g., an injection dosage form or an oral dosage form. The injection dosage form includes liquid injections, powder for injection, tablets for injection, and so forth. The oral dosage form includes tablets, capsules, oral liquid preparations, etc. In the case of a liquid injection, the mitoxantrone hydrochloride liposome contains 0.5 to 5 mg/ml, preferably 1 to 2 mg/ml, more preferably 1 mg/ml of an active ingredient in terms of mitoxantrone; when the prednisone is a tablet, the strength is 5 mg/tablet; when the cyclophosphamide is powder for injection, the strength is 0.2 g/vial, and it is formulated into 200 mg/10 ml of a solution when used; when the vincristine is powder for injection, the strength is 1 mg/vial, and it is formulated into 1 mg/20 ml of a solution when used.

Prednisone as a tablet with the strength of 5 mg/tablet means that each tablet contains 5 mg of prednisone; cyclophosphamide as power for injection with the strength of 0.2 g/vial means that each vial of the power for injection contains 0.2 g of cyclophosphamide; and vincristine as power for injection with the strength of 1 mg/vial means that each vial of the power for injection contains 1 mg of vincristine.

The medication may further contain an additional drug for treating PTCL, and the additional drug refers to those approved by drug administration departments in China or other countries and regions (e.g., the United States, the European Union, Japan, and South Korea) to treat PTCL.

The present disclosure provides a method for treating PTCL, wherein a PTCL patient is administered with a therapeutically effective dose of a mitoxantrone hydrochloride liposome and cyclophosphamide, vincristine, and prednisone.

The present disclosure further provides a method for improving an efficacy of a treatment regimen of cyclophosphamide, vincristine, and prednisone against PTCL, wherein a PTCL patient is further administered with a therapeutically effective dose of a mitoxantrone hydrochloride liposome in addition to administration of cyclophosphamide, vincristine, and prednisone.

The present disclosure further provides a method for improving an efficacy of a mitoxantrone hydrochloride liposome against PTCL, wherein a PTCL patient is further administered with therapeutically effective doses of cyclophosphamide, vincristine, and prednisone in addition to administration of a mitoxantrone hydrochloride liposome.

In the methods described above, the mitoxantrone hydrochloride liposome, the cyclophosphamide, and the vincristine are preferably administered by injection; and the prednisone is preferably administered orally. Preferably, the therapeutically effective dose of the mitoxantrone hydrochloride liposome is 8 to 30 mg/m$^2$, more preferably 12 to 24 mg/m$^2$ in terms of mitoxantrone; specifically, the therapeutically effective dose of the mitoxantrone hydrochloride liposome is, for example, 12 mg/m$^2$, 14 mg/m$^2$, 15 mg/m$^2$, 16 mg/m$^2$, 18 mg/m$^2$, 20 mg/m$^2$, or 24 mg/m$^2$. The dose of the cyclophosphamide is 750 mg/m$^2$; the dose of the vincristine is 1.4 mg/m$^2$ (the maximum dose per subject does not exceed 2 mg in terms of the body surface area); and the dose of the prednisone is 100 mg/d. Preferably, the administration cycle is once every 4 weeks or 3 weeks. In each administration cycle, the mitoxantrone hydrochloride liposome, cyclophosphamide, and vincristine are administered once, and the prednisone is administered 5 times consecutively. Preferably, a PTCL patient is administered with therapeutically effective doses of the mitoxantrone hydrochloride liposome, prednisone, vincristine, and cyclophosphamide in any sequential order on Day 1 of each administration cycle, and the prednisone continues to be administered from Day 2 to Day 5. Preferably, on Day 1 of each administration cycle, the prednisone is administered before the administration of the mitoxantrone hydrochloride liposome, the vincristine is administered after the administration of the mitoxantrone hydrochloride liposome, and the cyclophosphamide is then administered.

The present disclosure further provides a composition for treating PTCL, comprising a mitoxantrone hydrochloride liposome and cyclophosphamide, vincristine, and prednisone, wherein a PTCL patient is administered with therapeutically effective doses of the mitoxantrone hydrochloride liposome, prednisone, vincristine, and cyclophosphamide in any sequential order on Day 1 of each administration cycle, and the prednisone continues to be administered from Day 2 to Day 5. Preferably, on Day 1 of each administration cycle, the prednisone is administered before the administration of the mitoxantrone hydrochloride liposome, the vincristine is administered after the administration of the mitoxantrone hydrochloride liposome, and the cyclophosphamide is then administered. Preferably, the administration cycle is once every 4 weeks or 3 weeks. Preferably, the dose of the mitoxantrone hydrochloride liposome is 8 to 30 mg/m$^2$, more preferably 12 to 24 mg/m$^2$ in terms of the mitoxantrone. Preferably, the dose of the cyclophosphamide is 750 mg/m$^2$, the dose of the vincristine is 1.4 mg/m$^2$ (the maximum dose per subject does not exceed 2 mg in terms of the body surface area), and the dose of the prednisone is 100 mg/d.

The "administration in any sequential order" used herein means that the mitoxantrone hydrochloride liposome and the cyclophosphamide, vincristine, and prednisone are present in separate preparations, and administered separately in a clinically acceptable manner, without a mandatory regulation on the sequential order of administration; the respective drugs are not mixed in vitro.

The present disclosure further provides a medication for improving an efficacy of a treatment regimen of cyclophosphamide, vincristine, and prednisone in the treatment of PTCL, the medication containing a mitoxantrone hydrochloride liposome that is administered at any time after the prednisone is administered and before the vincristine and the cyclophosphamide are administered. Preferably, a PTCL patient is administered with therapeutically effective doses of the mitoxantrone hydrochloride liposome, prednisone, vincristine, and cyclophosphamide in any sequential order on Day 1 of each administration cycle, and the prednisone continues to be administered from Day 2 to Day 5. Preferably, on Day 1 of each administration cycle, the prednisone is administered before the administration of the mitoxantrone hydrochloride liposome, the vincristine is administered after the administration of the mitoxantrone hydrochloride liposome, and the cyclophosphamide is then administered. Preferably, the dose of the mitoxantrone hydrochloride liposome is 8 to 30 mg/m$^2$, more preferably 12 to 24 mg/m$^2$ in terms of the mitoxantrone, and the mitoxantrone hydrochloride liposome is administered once every 4 weeks or 3 weeks. Preferably, the dose of the cyclophosphamide is 750 mg/m$^2$, the dose of the vincristine is 1.4 mg/m$^2$ (the maximum dose per subject does not exceed 2 mg in terms of the body surface area), and the dose of the prednisone is 100 mg/d.

The present disclosure further provides a medication for improving an efficacy of a mitoxantrone hydrochloride liposome in the treatment of PTCL, wherein the medication contains cyclophosphamide, vincristine, and prednisone, and the mitoxantrone hydrochloride liposome is administered at any time after the prednisone is administered and before the vincristine and the cyclophosphamide are administered. Preferably, a PTCL patient is administered with therapeutically effective doses of the mitoxantrone hydrochloride liposome, prednisone, vincristine, and cyclophosphamide in any sequential order on Day 1 of each administration cycle, and the prednisone continues to be administered from Day 2 to Day 5. Preferably, on Day 1 of each administration cycle, the prednisone is administered before the administration of the mitoxantrone hydrochloride liposome, the vincristine is administered after the administration of the mitoxantrone hydrochloride liposome, and the cyclophosphamide is then administered. Preferably, the dose of the mitoxantrone hydrochloride liposome is 8 to 30 mg/m$^2$, more preferably 12 to 24 mg/m$^2$ in terms of the mitoxantrone, and the mitoxantrone hydrochloride liposome is administered once every 4 weeks or 3 weeks. Preferably, the dose of the cyclophosphamide is 750 mg/m$^2$, the dose of the vincristine is 1.4 mg/m$^2$ (the maximum dose per subject does not exceed 2 mg in terms of the body surface area), and the dose of the prednisone is 100 mg/d.

Preferably, for each intravenous administration, the infusion administration time of the liposome pharmaceutical preparation is 30 min to 120 min, preferably 60 min to 120 min, further preferably 90±15 min.

The doses of the mitoxantrone hydrochloride liposome according to the present disclosure are all calculated in terms of the mitoxantrone.

The mitoxantrone hydrochloride liposome according to the present disclosure may be prepared by a conventional method in the art, or it may be a mitoxantrone hydrochloride liposome prepared by any one of the methods disclosed in the prior arts, for example, prepared by the method disclosed in WO2008/080367A1, the entire contents of which are incorporated herein by reference.

In some examples, the mitoxantrone liposome according to the present disclosure has a particle size of about 30 to 80 nm, and contains: 1) mitoxantrone or its pharmaceutically acceptable salt as an active ingredient, which may form a poorly soluble precipitate with a multivalent counter ion in the liposome, and 2) a lipid bilayer containing a lipid with a phase transition temperature (Tm) higher than body temperature, so that the phase transition temperature of the liposome is higher than the body temperature. The lipid with a Tm higher than the body temperature is phosphatidylcholine, hydrogenated soybean phosphatidylcholine, hydrogenated egg-yolk phosphatidylcholine, dipalmitoyl phosphatidylcholine or distearoyl phosphatidylcholine or any combination thereof, preferably, the mitoxantrone liposome has a particle size of about 35 to 75 nm, preferably 40 to 70 nm, further preferably 40 to 60 nm, particularly preferably 60 nm. In some examples, the lipid bilayer contains hydrogenated soybean phosphatidylcholine, cholesterol, and polyethylene glycol 2000-modified distearoyl phosphatidylethanolamine at a mass ratio of 3:1:1, the particle size of the liposome is about 60 nm, and the counter ion is a sulfate ion.

In some examples, the mitoxantrone hydrochloride liposome according to the present disclosure is prepared by the following method: HSPC (hydrogenated soybean phosphatidylcholine), Chol (cholesterol), and DSPE-PEG2000 (polyethylene glycol 2000-modified distearoyl phosphatidylethanolamine) are weighed at a (3:1:1) mass ratio, and dissolved in 95% ethanol to obtain a clear solution (i.e., the solution of lipids in ethanol). The solution of lipids in ethanol is mixed with 300 mM ammonium sulfate solution, shaken and hydrated at 60° to 65° C. for 1 h to obtain a heterogeneous multilamellar liposome. Thereafter, the particle size of the liposome is reduced using a microfluidizer. The resulting sample is diluted 200 times with a 0.9% NaCl solution, and then detected with NanoZS. The average particle size of the particles is about 60 nm, and the main peak is concentrated between 40 nm and 60 nm. Afterwards, an ultrafiltration device is used to remove the ammonium sulfate from the outer phase of the blank liposome, and the outer phase is replaced with 290 mM sucrose and 10 mM glycine, so as to form a transmembrane ammonium sulfate gradient. A mitoxantrone hydrochloride solution (10 mg/mL) is added to the blank liposome at a lipid:drug ratio of 16:1, and the drug is loaded at 60° C. to 65° C. After incubation for about 1 h, the encapsulation efficiency is proved by the gel exclusion chromatography to be about 100%. The product resulting from this method is named PLM 60. The weight ratio of HSPC:Chol:DSPE-PEG2000: mitoxantrone in the PLM60 is 9.58:3.19:3.19:1, and the osmotic pressure of the sucrose-glycine solution is close to the physiological value.

Advantageous Effects

The combined administration of the mitoxantrone hydrochloride liposome of the present disclosure and cyclophosphamide, vincristine, and prednisone is safe and tolerable for patients, has small toxicity and side effects, and can result in a high ORR in treatment-naïve PTCL patients. The efficacy is expected to be further improved with the increase of the administration cycle, thereby improving the progression-free survival (PFS) and 5-year overall survival (OS) of patients.

DETAILED DESCRIPTION

The Example described below is the specific description of the present disclosure and should not be construed as a limitation to the scope of the present disclosure.

Example 1 Clinical Study on the Treatment of Treatment-Naïve PTCL by the Liposome Injection of Mitoxantrone Hydrochloride Combined with Cyclophosphamide, Vincristine, and Prednisone This study was a single-arm, open-label and multicenter Phase Ib clinical study, into which treatment-naïve PTCL subjects were incorporated and administered with different doses of the liposome injection of mitoxantrone hydrochloride and fixed doses of cyclophosphamide, vincristine, and prednisone. This study was intended to explore the safety and tolerance of the treatment regimens described above, determine the optimal dosage of the liposome injection of mitoxantrone hydrochloride used in this combined administration regimen, while evaluating the efficacy and observing the pharmacokinetic characteristics. This study was divided into a dose-escalation phase and a dose-expansion phase.

I. Design of Trials

1. Dose-Escalation Phase (1) Overall Design

The study included a screening period, a treatment period and a follow-up period.

Subjects signed the Informed Consent Form and completed all baseline assessments within the screening period. Eligible subjects would enter the treatment period. The dosage of the liposome injection of mitoxantrone hydrochloride would be gradually escalated from a low-dose group to a high-dose group with every 4 W (28 days) as a cycle. DLT was observed in the first administration cycle. All subjects were subjected to the collection of blood samples for PK analysis at different time points before and after the administration according to the protocol, and completed the relevant examinations specified in the protocol during the treatment, so as to observe the safety, tolerance, and efficacy. The same subject could only receive the treatment and administration schedule of one dose regimen during the study. Subjects entered the follow-up period at the end of the treatment period.

(2) Dose Escalation and Administration Regimen

During the dose-escalation phase of mitoxantrone hydrochloride liposome (PLM 60), 12 mg/m$^2$ (in terms of mitoxantrone) was taken as the initial dose; three dose groups (12 mg/m$^2$, 15 mg/m$^2$, and 18 mg/m$^2$) were preset; and PLM 60 was administered via intravenous infusion on Day 1 (D1) of each cycle.

Vincristine: the dose was 1.4 mg/m$^2$ (in terms of the body surface area, the maximum dose per subject did not exceed 2 mg); it was administered via intravenous injection on D1 after the administration of the mitoxantrone hydrochloride liposome.

Cyclophosphamide: the dose was 750 mg/m$^2$; it was administered via intravenous infusion on D1 after the administration of the mitoxantrone hydrochloride liposome and vincristine.

Prednisone: the dose was 100 mg/d; it was orally administered from D1 to D5, and administered before the administration of the mitoxantrone hydrochloride liposome on D1; only prednisone was administered from D2 to D5 as long as the administration was in accordance with the clinical administration requirements for prednisone when used alone.

Once DLT occurred in a subject, the original treatment regimen would be discontinued. Corresponding treatment would be provided by the investigators according to the standard for clinical diagnosis and treatment, and the subject was monitored until the toxicity returned to ≤Grade 1 or the baseline level. If the investigators determined that the benefits gained by the subject from the continuation of the treatment with the original regimen overweighed the risks, the subject could resume his/her treatment period (the dosage was the same as the original dose) with the consent of the sponsor; if the investigators determined that it was inappropriate to keep on treating the subject with the original regimen, the subject was withdrawn from the study.

(3) Provisions for the Continuation of the Administration

1) The following requirements needed to be satisfied: neutrophil count ≥1.5×10$^9$/L hemoglobin ≥80 g/L, and platelet count ≥75×10$^9$/L.

2) Non-hematological toxicity (except alopecia) must return to ≤Grade 1 or the baseline level, regardless of whether a medicament was administered for the treatment of drug toxicity.

3) If the conditions described above could not be met, the dose was not reduced in principle and the administration might be delayed for no more than 14 days.

4) If the toxicity did not return to the level that met the administration conditions as required in 1) and 2) and/or the administration was delayed for more than 14 days, the administration might be continued after communication with the sponsor, provided that the investigators determined that the subject could still benefit from the administration.

2. Dose-Expansion Phase

After the recommended phase II dose (RP2D) of the mitoxantrone hydrochloride liposome in the combined regimen of the mitoxantrone hydrochloride liposome, cyclophosphamide, vincristine and prednisone was determined based on the research results of the dose-escalation phase, the dose-expansion phase might be initiated.

The study included a screening period, a treatment period, and a follow-up period. The liposome injection of mitoxantrone hydrochloride was expanded with the dose of RP2D, and the doses of cyclophosphamide, vincristine, and prednisone were the same as those used at the escalation phase. The treatment was carried out in two groups, i.e., a Q4W (28 days) group and a Q3W (21 days) group, with an increase of 10 to 20 cases in each group.

Eligible subjects were screened according to the study procedure, and enrolled into the Q4W group or the Q3W group respectively via cross-over enrollment. During the treatment, every 28 days were a cycle for the Q4W group, and every 21 days were a cycle for the Q3W group. The administration was planned to be carried out for 6 cycles until the completion of 6 cycles of treatment or the appearance of the following situations, i.e., the progression of the disease, death, intolerable toxicity, need for other treatments (including changing chemotherapy regimen, ASCT, radiotherapy, etc.) in the opinion of the investigators, or voluntary withdrawal of the subject from the treatment (whichever occurred first). During the treatment, blood sampling for PK analysis and relevant examinations were carried out according to the requirements of the protocol, so as to observe the safety and efficacy. Subjects entered the follow-up period at the end of the treatment period.

3. End Date of the Study

The last subject completing his/her last follow-up visit was defined as the end of the study.

II. Test Population (I) Inclusion Criteria

Patients who met all of the following criteria were eligible for the enrollment of this study:

1. patients who had a sufficient understanding of this study, voluntarily participated in this study and signed the Informed Consent Form (ICF);

2. aged between 18 and 70 (inclusive of the upper limit and the lower limit);

3. treatment-naïve PTCL being histopathologically confirmed as one of the following subtypes:

(1) peripheral T-cell lymphoma, not otherwise specified (PTCL-NOS);

(2) angioimmunoblastic T-cell lymphoma (AITL);

(3) anaplastic large T-cell lymphoma (ALCL), ALK+;

(4) anaplastic large T-cell lymphoma (ALCL), ALK−; and

(5) other subtypes of PTCL deemed by the investigators to be eligible for the enrollment and approved by the sponsor;

4. PTCL, of which the affinity to fluorodeoxyglucose (FDG) could be evaluated by PET/CT;

5. ECOG score: 0 to 1;

6. the laboratory examination meeting the following criteria:

(1) absolute neutrophil count (ANC) ≥1.5×10$^9$/L;

(2) platelet (PLT) ≥75×10$^9$/L;

(3) hemoglobin (HB) ≥80 g/L;

(4) total serum bilirubin (TBIL) ≤1.5 times the upper limit of normal (ULN);

(5) alanine aminotransferase (ALT) and aspartate aminotransferase (AST) ≤2.5 times the ULN; and (6) serum creatinine (Scr) 51.5 times the ULN;

7. female subjects necessarily meeting one of the following conditions:

(1) postmenopausal subjects having gone through menopause for at least 1 year; and (2) subjects of childbearing age being required to meet the following conditions:

a) the result of blood pregnancy test being negative prior to the enrollment in this trial; and b) consenting to take a recognized and very effective contraceptive measure [defined as being able to be taken persistently and correctly with an annual failure rate of less than 1%, for example, combined hormone (including estrogen and progesterone) combined with ovulation inhibition, progesterone contraception combined with ovulation inhibition, intrauterine device (IUD), intrauterine system (IUS), bilateral tubal ligation, or vasectomy] during the entire study period and within at least 12 months after the completion of the last administration;

8. male subjects or their partners consenting to take one of the very effective contraceptive measures described in Item 7 during the study so as to realize effective contraception during the entire treatment period and within at least 12 months after the completion of the last administration.

(II) Exclusion Criteria

Subjects who met any one of the following exclusion criteria were ineligible for this study:

1. Histopathology being one of the following subtypes:

(1) extranodal NK/T-cell lymphoma, nasal type (NKTCL);

(2) mycosis fungoides (MF)/Sézary syndrome (SS) and primary cutaneous T-cell lymphoma such as primary cutaneous anaplastic large cell lymphoma; and (3) leukemic PTCL such as adult T-cell leukemia/lymphoma.

2. Patients at the lymphocytic leukemia stage (the proportion of lymphoma cells was ≥20% in bone marrow examination), or with involvement of central nervous system (CNS), or complicated with hemophagocytic syndrome.

3. Expected survival time <6 months.

4. Subjects with a history of allergy to anthracyclines or liposome-based drugs.

5. Subjects with contraindications for the administration of cyclophosphamide, vincristine, or prednisone.

6. Subjects having received anti-lymphoma therapy, except for short-term or low-dose administration of glucocorticoids (the short-term administration of glucocorticoids was defined as prednisone (or in terms of prednisone) being administered at a dose of ≤100 mg/d for less than 7d; the low-dose administration of glucocorticoids was defined as prednisone (or in terms of prednisone) being administered at a dose of ≤30 mg/d).

7. Subjects with impaired heart function or significant heart disease, including but not limited to:

(1) suffering from myocardial infarction, congestive heart failure and viral myocarditis within 6 months prior to the screening; suffering from heart diseases with symptoms required to be treated or intervened, such as unstable angina pectoris and arrhythmia;

(2) heart functions ranging from Class II to Class IV (New York Heart Association (NYHA) Functional Classification);

(3) the heart's ejection fraction (EF) detected by ultrasonic cardiogram being lower than 50% or the lower limit specified by the research center;

(4) persistent history of cardiomyopathy; and (5) QTc>450 ms, or suffering from congenital QT prolongation syndrome.

8. Subjects having positive hepatitis B surface antigen and an HBV-DNA titer higher than the upper limit specified by the research center, or subjects having positive hepatitis C (HCV) antibody, or subjects having positive human immunodeficiency virus (HIV) antibody detected in preliminary screening.

9. Subjects having undergone major surgery within 4 to 6 weeks prior to the screening or expected to undergo a major surgery during the study period.

10. Subjects suffering from serious infection within 4 weeks prior to the screening and determined by the investigators as not suitable for chemotherapy.

11. Subjects with poorly controlled hypertension during the screening.

12. Subjects with poorly controlled diabetes during the screening.

13. Subjects with a history of active visceral haemorrhage within 3 months prior to the screening.

14. Subjects with a history of malignancy within five years, which might affect the implementation of the trial protocol or the analysis of the results (except for cured skin basal cell carcinoma, cervical carcinoma in situ, breast carcinoma in situ, gastrointestinal intramucosal carcinoma in situ, and localized prostate cancer).

15. Subjects having undergone the solid organ transplantation.

16. Subjects with a history of mental disease or cognitive disorder.

17. Subjects with a history of drug abuse (using narcotic drugs or psychotropic drugs for non-medical purpose) and a history of drug dependence (sedative hypnotics, analgesics, anesthetics, stimulants and psychotomimetic drugs, etc.).

18. Pregnant or nursing women.

19. Subjects deemed by the investigators to be inappropriate to participate in this study.

III. Research Results

The study were currently at the dose-escalation phase, and had completed the escalations of the three preset dose groups of 12 mg/m$^2$, 15 mg/m$^2$, and 18 mg/m$^2$, without causing a cease of dose escalation. After the communication and discussion between the investigators and the sponsor, a 21 mg/m$^2$ dose group was added (in which 3 cases had been enrolled).

Efficacy evaluation was conducted by PET-CT according to the Lugano 2014 criteria.

A total of 22 treatment-naïve PTCL subjects were enrolled in this study, of which 18 subjects were under treatment and 4 subjects withdrew from the study (of which 3 subjects withdrew due to the progression of the disease and 1 subject withdrew due to poor efficacy). Among them, 13 subjects who had undergone one efficacy evaluation (84 days) were enrolled for the following observations.

The doses of the mitoxantrone hydrochloride liposome (PLM 60) were listed in Table 1 below;

the dose of vincristine (strength of the powder for injection: 1 mg/vial) was 1.4 mg/m², and it was administered via intravenous injection on Day 1 of each cycle after the administration of the mitoxantrone hydrochloride liposome;

the dose of cyclophosphamide (strength of the powder for injection: 0.2 g/vial) was 750 mg/m², and it was administered via intravenous infusion on Day 1 of each cycle after the administration of the mitoxantrone hydrochloride liposome and vincristine; and the dose of prednisone (strength of the tablet: 5 mg/tablet) was 100 mg/d, and it was orally administered from Day 1 to Day 5 of each cycle, and administered before the administration of the mitoxantrone hydrochloride liposome on Day 1 of each cycle; only prednisone was administered from Day 2 to Day 5 of each cycle.

The evaluation results were as shown in Table 1 below.

TABLE 1

| Dose | 12 mg/m² | 15 mg/m² | 18 mg/m² | Total |
|---|---|---|---|---|
| Subjects | 6 cases | 6 cases | 1 case | 13 cases |
| CR (complete remission) | 0 case | 1 case | 1 case | 2 cases |
| PR (partial remission) | 4 cases | 3 cases | 0 case | 7 cases |
| SD (stable disease) | 2 cases | 1 case | 0 case | 3 cases |
| PD (progression of disease) | 0 case | 1 case | 0 case | 1 case |
| CR | 0% | 16.7% (1/6) | 100% (1/1) | Total CR: 15% (2/13) |
| ORR (objective remission rate) | 67% (4/6) | 67% (4/6) | 100% (1/1) | Total ORR: 69% (9/13) |

Results: The combined administration of the mitoxantrone hydrochloride liposome of the present disclosure and cyclophosphamide, vincristine, and prednisone at the doses described above was safe and tolerable with small toxicity and side effects and could gain a higher total ORR in treatment-naïve PTCL patients, and the efficacy tended to increase with the increase of the dose of the mitoxantrone liposome. Most patients had only undergone one efficacy evaluation so far. The efficacy was expected to be further improved with the increase of the administration cycle. Among them, the efficacy of the high-dose mitoxantrone hydrochloride liposome group would be superior to that of the clinical standard treatment (CHOP-based regimen).

What is claimed is:

1. A method for treating treatment-naïve peripheral T-cell lymphoma (PTCL), comprising administering a therapeutically effective dose of a mitoxantrone liposome, cyclophosphamide, vincristine, and prednisone to a treatment-naïve PTCL patient in need thereof, wherein the mitoxantrone liposome is a mitoxantrone hydrochloride liposome, and the therapeutically effective dose of the mitoxantrone hydrochloride liposome is 18 to 30 mg/m² in terms of mitoxantrone; the therapeutically effective dose of the cyclophosphamide is 750 mg/m², the therapeutically effective dose of the vincristine is 1.4 mg/m², and the therapeutically effective dose of the prednisone is 100 mg/d.

2. The method according to claim 1, wherein the mitoxantrone hydrochloride liposome, the prednisone, the cyclophosphamide, and the vincristine may be present in the same preparation or in separate preparations; when these four drugs are present in separate preparations, their dosage forms may or may not be the same; when the mitoxantrone hydrochloride liposome is a liquid injection, the mitoxantrone hydrochloride liposome contains 0.5 to 5 mg/ml of an active ingredient in terms of mitoxantrone; when the prednisone is a tablet, the strength is 5 mg/tablet; when the cyclophosphamide is powder for injection, the strength is 0.2 g/vial; and when the vincristine is powder for injection, the strength is 1 mg/vial.

3. The method according to claim 1, further comprising administering an additional drug for treating the PTCL.

4. The method according to claim 1, wherein a PTCL patient is administered with a therapeutically effective dose of a mitoxantrone hydrochloride liposome and cyclophosphamide, vincristine, and prednisone; the mitoxantrone hydrochloride liposome, the cyclophosphamide, and the vincristine are administered by injection; and the prednisone is administered orally.

5. The method according to claim 1, wherein the mitoxantrone hydrochloride liposome, cyclophosphamide, vincristine, and prednisone are administered in an administration cycle and the administration cycle is once every 4 weeks or 3 weeks, the mitoxantrone hydrochloride liposome is administered, on the first day of each administration cycle, at any time after the prednisone is administered and before the vincristine and the cyclophosphamide are administered, and is administered once every 4 weeks or 3 weeks at a dose of 18 to 30 mg/m².

6. The method according to claim 1, wherein the mitoxantrone hydrochloride liposome has a particle size of about 30 to 80 nm, and contains: 1) mitoxantrone hydrochloride as an active ingredient, and 2) a lipid bilayer containing a lipid, wherein the lipid is phosphatidylcholine, hydrogenated soybean phosphatidylcholine, hydrogenated egg-yolk phosphatidylcholine, dipalmitoyl phosphatidylcholine or distearoyl phosphatidylcholine or any combination thereof.

7. The method according to claim 2, wherein the mitoxantrone hydrochloride liposome contains 1 to 2 mg/ml of an active ingredient in terms of mitoxantrone.

8. The method according to claim 1, wherein the mitoxantrone hydrochloride liposome is administered at a dose of 18 to 24 mg/m².

* * * * *